United States Patent [19]

Bonse et al.

[11] 4,315,094
[45] Feb. 9, 1982

[54] PREPARATION OF 4-AMINO-6-TERT-BUTYL-3-ALKYL-THIO-1,2,4-TRIAZIN-5(4H)-ONE

[75] Inventors: Gerhard Bonse, Cologne; Heinz U. Blank, Odenthal; Hans Krätzer, Wuppertal, all of Fed. Rep. of Germany

[73] Assignee: Bayer Aktiengesellschaft, Leverkusen, Fed. Rep. of Germany

[21] Appl. No.: 235,495

[22] Filed: Feb. 19, 1981

[30] Foreign Application Priority Data

Mar. 8, 1980 [DE] Fed. Rep. of Germany ....... 3008921

[51] Int. Cl.$^3$ .......................................... C07D 253/06
[52] U.S. Cl. ......................,................... 544/182
[58] Field of Search ........................... 544/182

[56] References Cited

U.S. PATENT DOCUMENTS 4,175,188 11/1979 Klenk et al. ................... 544/182

Primary Examiner—John M. Ford
Attorney, Agent, or Firm—Sprung, Felfe, Horn, Lynch & Kramer

[57] ABSTRACT

In the preparation of 4-amino-6-tert.-butyl-3-alkylthio-1,2,4-triazin-5-(4H)-one of the formula

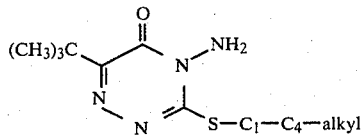

wherein (1) pivaloyl cyanide of the formula

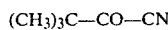

$(CH_3)_3C-CO-CN$ is reacted to form a derivative of pyruvic acid, (2) the pyruvic acid derivative is condensed with thiocarbohydrazide of the formula

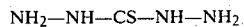

$NH_2-NH-CS-NH-NH_2$ to form 4-amino-6-tert.-butyl-3-mercapto-1,2,4-triazin-5(4H)-one of the formula

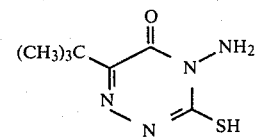

and (3) this is alkylated, the improvement which comprises effecting step (1) by reaction with a carboxylic acid anhydride of the formula

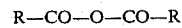

$R-CO-O-CO-R$ in which R is an optionally substituted aliphatic radical with up to 8 carbon atoms or an optionally substituted phenyl radical, in the presence of a strong acid at a temperature between about $-50°$ and $+150°$ C., and then adding water to the reaction mixture, thereby to form trimethylpyruvic acid N-acylamide of the formula

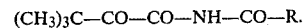

$(CH_3)_3C-CO-CO-NH-CO-R.$

24 Claims, No Drawings

PREPARATION OF 4-AMINO-6-TERT.-BUTYL-3-ALKYLTHIO-1,2,4-TRIAZIN-5(4H)-ONE

The present invention relates to an unobvious process for the preparation of 4-amino-6-tert.-butyl-3-methylthio-1,2,4-triazin-5(4H)-one, which is known as a herbicide.

Processes for the preparation of 4-amino-6-tert.-butyl-3-methylthio-1,2,4-triazin-5(4H)-one (I) starting from pivaloyl cyanide or other pivalic acid derivatives have already been disclosed. They differ in the method of the preparation of the intermediate product 4-amino-6-tert.-butyl-3-mercapto-1,2,4-triazin-5(4H)-one (VI).

According to German Published Specification DE-OS No. 2,165,554, the triazinone (I) can be prepared by reacting pivaloyl chloride with an isonitrile, hydrolyzing the imide-chloride formed to give the corresponding trimethylpyruvic acid amide, reacting the amide further with thiocarbohydrazide and methylating the resulting cyclisation product (VI) (yields: 60–82% of theory of (VI); 49–67% of (I), in each case relative to pivaloyl chloride).

According to U.S. Ser. No. 356,531, filed May 3, 1973, it is possible to prepare the said triazinone (I) by a process in which a pivalic acid amide, for example pivalanilide, is converted into the corresponding pivalimido-chloride by chlorination, for example by means of thionyl chloride, this product is reacted with a metal cyanide, for example copper(I) cyanide, or hydrogen cyanide, if appropriate in the presence of a catalyst, to give the corresponding α-imino-nitrile, the latter is cyclized to 4-amino-6-tert.-butyl-5-imino-3-mercapto-1,2,4-triazine by reaction with thiocarbohydrazide, the 5-imino group is then hydrolyzed to the 5-keto group, the intermediate product (VI) being obtained, and this intermediate product is then methylated (yields: 42–57% of theory of (VI); 35–47% of theory of (I), in each case relative to pivalanilide).

Both processes require an exceptional degree of technical effort and proceed with unsatisfactory yields, and are thus unsuitable for application on a large industrial scale.

According to U.S. Pat. No. 4,175,188, the said triazinone (I) can be prepared by a process in which pivaloyl cyanide is reacted with t-butanol or isobutylene in a so-called Ritter reaction to give trimethylpyruvic acid N-t-butylamide and this is cyclized, if appropriate after prior hydrolysis to the free trimethylpyruvic acid, with thiocarbohydrazide to give the intermediate product (VI), and the latter is then methylated (yields: 51–67% of theory of (VI); 41–54% of (I), in each case relative to pivoloyl cyanide).

The process last mentioned has the fundamental disadvantage that the trimethylpyruvic acid N-t-butylamide obtained as the intermediate product can be reacted further only with relative difficulty; this applies both to the hydrolysis to the free keto-acid and to the cyclization reaction with thiocarbohydrazide.

Acid hydrolysis of trimethylpyruvic acid N-t-butylamide to give trimethylpyruvic acid is thus effected, in a yield of only 75% of theory, by heating under reflux in 5N HCl for 10 hours and subsequent working up by extraction with $CH_2Cl_2$, dilute aqueous NaOH solution, concentrated hydrochloric acid and ethyl acetate.

If prior hydrolysis of the α-keto-carboxylic acid N-t-butylamide is dispensed with and this is reacted directly with thiocarbohydrazide, the cyclization product 4-amino-6-t-butyl-3-mercapto-1,2,4-triazin-5-(4H)-one can be isolated in yields of only 72% of theory after heating under reflux for several hours (up to 8 hours). Moreover, experiments have shown that the reaction of α-keto-carboxylic acid N-alkylamides with thiocarbohydrazide according to German Published Specification DE-OS No. 2,165,554 and U.S. Pat. No. 4,175,188 does not proceed to give 4-amino-6-t-butyl-3-mercapto-1,2,4-triazin-5(4H)-one as a single product, but proceeds with the formation of numerous by-products.

The present invention now provides a process for the preparation of 4-amino-6-tert.-butyl-3-methylthio-1,2,4-triazin-5(4H)-one of the formula

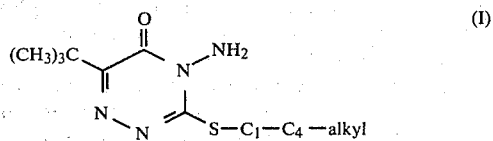

in which, in a first stage, pivaloyl cyanide of the formula $$(CH_3)_3C—CO—CN \qquad (II)$$

is reacted with a carboxylic acid anhydride of the general formula $$R—CO—O—CO—R \qquad (III),$$

in which R represents an optionally substituted aliphatic radical with up to 8 carbon atoms or an optionally substituted phenyl radical, in the presence of a strong acid and if appropriate in the presence of a solvent, at a temperature between about −50° and +150° C., and water is then added to the reaction mixture and, in a second stage, the trimethylpyruvic acid N-acylamide which is thereby formed, of the general formula $$(CH_3)_3C—CO—CO—NH—CO—R \qquad (IV),$$

in which R has the abovementioned meaning, is reacted, if appropriate after prior hydrolysis to the free trimethylpyruvic acid of the formula $$(CH_3)_3C—CO—COOH \qquad (V),$$

with thiocarbohydrazide ($NH_2$—NH—CS—NH—$NH_2$) at a temperature of about −20° to +150° C. to give 4-amino-6-tert.-butyl-3-mercapto-1,2,4-triazin-5-(4H)-one of the formula

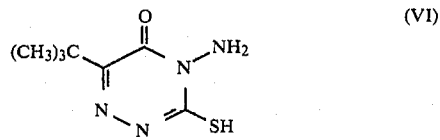

and, in a third stage, this intermediate product (VI) is alkylated (which can be effected in the customary manner).

By means of the present invention the compound (I) can be obtained, starting from pivaloyl cyanide, in a high yield and in high purity in a suprisingly simple manner.

Compared with the state of the art, the first stage of the process according to the invention is a novel and advantageous procedure, in which the trimethylpyruvic acid N-acylamides (IV) are formed in a surprisingly smooth and uniform reaction. The compounds (IV) have not hitherto been disclosed in the literature.

Whereas the preparation of N-acylamides by reacting nitriles with carboxylic acids or anhydrides thereof in the presence of catalysts, for example mineral acids, is described for a number of aliphatic and aromatic nitriles (see Compr. Org. Che. 2, page 539 (1979)), the corresponding conversion in the class of acyl cyanides to give α-keto-carboxylic acid N-acylamides was hitherto unknown.

The reaction of the trimethylpyruvic acid N-acylamides (IV), which are readily accessible according to the invention, with thiocarbohydrazide already takes place under mild conditions and leads to a high yield of very pure 4-amino-6-tert.-butyl-3-mercapto-1,2,4-triazin-5(4H)-one (VI).

The process according to the invention avoids the abovementioned disadvantages associated with the comparable processes which are already known for the preparation of the herbicidal active compound (I); this means a considerable technical simplification.

Compared with other processes, which are already known (see for example, U.S. Pat. Nos. 3,752,808, 4,113,768, and 4,028,409 for the preparation of the active compound (I) from other pivalic acid derivatives or pinacoline, the process according to the invention likewise has the industrial advantage of being highly simplified. Compared wtih the processes starting from pinacoline, the different raw material basis is to be regarded as an additional advantage.

If, in the first stage of the process, acetic anhydride is used as the carboxylic acid anhydride of the general formula (III) and concentrated sulphuric acid is used as the strong acid, the N-acetylamide intermediate product (IVa) is reacted as such with thiocarbohydrazide in the second stage, and, in the third stage, methyl bromide is used as the methylating agent, the course of the reaction in the process according to the invention can be illustrated by the following equation:

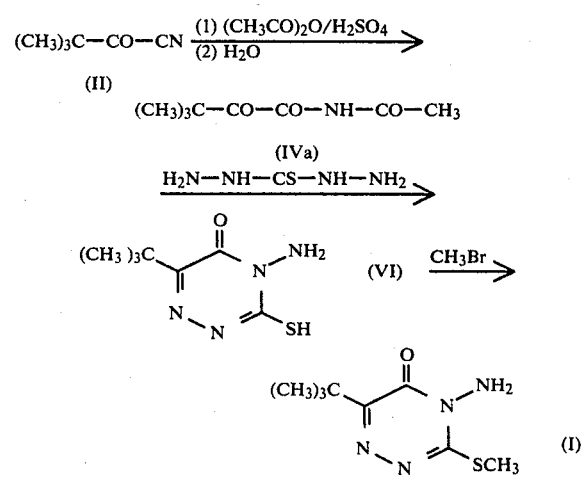

The pivaloyl cyanide (II) used as the starting material is known and can be prepared, for example, by reacting pivaloyl chloride with copper(I) cyanide (see, for example, J. Amer. Chem. Soc. 72, page 2793 (1950)).

Formula (III) provides a general definition of the carboxylic acid anhydrides also to be employed as starting substances. In this formula, R preferably represents optionally chlorine-substituted alkyl with 1 to 4 carbon atoms or phenyl.

The carboxylic acid ahydrides of the formula (III) are in some cases available on a large industrial scale, or they can be prepared by generally known methods, for example from the corresponding carboxylic acids.

Acetic anhydride, propionic anhydride and the anhydrides of chloroacetic acids are particularly preferred carboxylic acid anhydrides in the context of this invention.

In detail, the following statements may further be made regarding stage 1 of the process according to the invention:

The first stage of the process is carried out in the presence of a strong acid. Possible strong acids include inorganic oxyacids, such as concentrated sulphuric acid, perchloric acid, nitric acid and phosphoric acid, and also Lewis acids, such as boron trifluoride, aluminum chloride or zinc chloride. Aliphatic and aromatic sulphonic acids and phosphonic acids and halogenoalkanecarboxylic acids, for example trichloroacetic acid, are also suitable. It is also possible to carry out the reaction in the presence of several such acids. An oxyacid, especially concentrated sulphuric acid, is preferably used.

The reaction temperatures can be varied within a substantial range in this stage of the process. In general, the reaction is carried out, as indicated above, at temperatures between −50° and +150° C., preferably between 0° and 100° C. It is expedient to carry out the subsequent working up by means of ice-water.

The reaction is in general carried out under normal pressure.

The reaction in stage 1 of the process can be carried out in the absence or in the presence of a solvent or solubilizing agent. Possible solubilizing agents are certain organic solvents: particularly suitable solvents are glacial acetic acid and methylene chloride, and also dialkyl ethers, such as diethyl ether or di-isopropyl ether, and diaryl ethers, for example diphenyl ether.

In carrying out the first stage of the process according to the invention, about 0.5 to 10 mols, preferably about 0.8 to 4 mols, of carboxylic acid anhydride of the formula (III) are in general employed per mol of pivaloyl cyanide of the formula (II); a molar ratio of pivaloyl cyanide (II) to carboxylic acid anhydride (III) of about 1:1 to 1:2 is particularly preferred.

The acids required for carrying out the first stage of the process according to the invention are employed in catalytic amounts to amounts greater than the stoichiometric amount. In general, 0.5 to 10 mols, preferably 0.8 to 8 mols and particularly preferably 1 to 4 mols, of acid are employed per mol of pivaloyl cyanide (II).

A molar ratio of carboxylic acid anhydride (III) to acid of 1:2 is particularly advantageous.

This means that a molar ratio of pivaloyl cyanide (II) to carboxylic acid anhydride (III) to acid of 1:1:2 to 1:2:4 is very particularly favorable.

It is expedient to carry out the first stage of the process by a procedure in which the acid and the carboxylic acid anhydride (III), or a mixture of solvent, acid and carboxylic acid anhydride (III), are initially introduced into the reaction vessel and the pivaloyl cyanide (II) is added, if appropriate in a solvent.

The reaction times are in general 1 to 10 hours. It is most expedient subsequently to pour the reaction mixture onto ice. The trimethylpyruvic acid N-acylamides formed can be isolated by filtration or by extraction.

Extraction agents which are suitable here are solvents which are not miscible with water in all proportions, for example ethers, such as diethyl ether or diisopropyl ether; esters, for example ethyl acetate; ketones, for example methyl isobutyl ketone; halogenated hydrocarbons, for example methylene chloride, chlorobenzene or dichlorobenzene, and also aromatics, for example benzene, toluene, o-xylene, ethylbenzene, cumene or nitrobenzene. Methylene chloride is preferably used.

If desired, the trimethylpyruvic acid N-acylamides (IV) formed in the first stage of the process can easily be subjected to acid hydrolysis to give the free trimethylpyruvic acid (3,3-dimethyl-2-oxo-butyric acid) (V).

The reaction of the free trimethylpyruvic acid (V) with thiocarbohydrazide to give the cyclization product (VI) is known (see, for example, U.S. Pat. No. 4,113,767.

However, in the second stage of the process according to the invention, the new trimethylpyruvic acid N-acylamides (IV) are preferably reacted directly, that is to say without prior hydrolysis thereof to the free acid (V), with thiocarbohydrazide to give the compound (VI). This reaction is carried out, for example, in an aqueous solution containing mineral acid, preferably hydrochloric acid, or an aqueous-alcoholic solution containing mineral acid.

The reaction temperature can be varied within a substantial range in this stage of the process. In general, the reaction is carried out between −20 and +150° C., preferably between 0° and 100° C.

The starting substances are preferably employed in equimolar amounts in carrying out the second stage of the process. The intermediate product (VI) may be isolated in the customary manner., The intermediate product (VI) can also exist in the form of the tautomeric 4-amino-6-tert.-butyl-5-oxo-3-thioxotetrahydro-1,2,4(2H,4H)-triazine of the formula

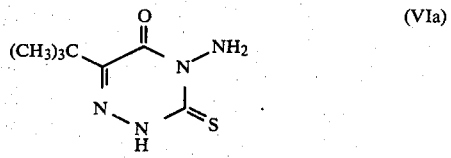

For simplicity, however, the term "4-amino-6-tert.-butyl-3-mercapto-1,2,4-triazin-5(4H)-one (VI)" is always used for the two tautomers (VI) and (VIa) in this description.

The third stage of the process according to the invention is carried out in a known manner, by reaction of (VI) with an alkylating agent, for example methyl bromide or methyl iodide, in the presence of a base, such as sodium hydroxide, in aqueous solution at a temperature between 0° and 50° C.

The 4-amino-6-tert.-butyl-3-methylthio-1,2,4-triazin-5(4H)-one of the formula (I) (Metribuzin) which can be prepared according to the invention is distinguished, as is known, by an outstanding herbicidal activity (see, for example, German Pat. No. 1,795,784).

The active compound prepared according to the invention influences plant growth and can therefore be used as a defoliant, desiccant, agent for destroying broad-leaved plants, germination inhibitor and, especially, as a weedkiller. By "weeds" in the broadest sense there are meant plants growing in places where they are not desired.

Whether the compound prepared according to the invention acts as total herbicide or selective herbicide depends essentially on the amount used.

The active compound prepared according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound prepared according to the present invention may be used, for example, as a selective herbicide in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compound is in no way restricted to these genera but also embraces other plants, in the same way.

Depending on the concentration, the compound can be used for the total combating of weeds, for example on industrial terrain and railway tracks and on paths and squares with or without trees. Equally, the compound can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

For combating weeds, the active compund can be used, as such or as a formulation, in admixture with other herbicides, it being possible to use finished formulations or tank mixing.

The active compound can be converted into the customary formulations, such as solutions, emulsions, suspensions, powders, foams, granules, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dystuffs, such as alizarin dyestuffs, azo dystuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight The active compound can be present in the formulations as a mixture with other active compounds, such as fungicides, insecticides, acaricides, nematicides, bird repellants, growth factors, plant nutrients and agents which improve soil structure.

The active compound can be used as such, in the form of its formulations or in the use forms prepared therefrom by further dilution, such as ready-to-use solutions, suspensions, emulsions, powders and granules. They may be used in the customary manner, for example by watering, spraying, atomizing or scattering.

The active compound prepared according to the invention can be applied either before or after emergence of the plants. It can also be incorporated into the soil before sowing.

The amount of active compound used can vary within a substantial range. It depends essentially on the nature of the desired effect. In general, the amounts used are between 0.05 to 10 kg of active compound per hectare, Preferably between 0.1 and 5 kg/ha.

The present invention also provides a herbicidal composition containing as active ingredient the compound prepared according to the present invention in admixture with a solid diluent or carrier or in admixture with a liquid diluent or carrier containing a surface-active agent.

The present invention also provides a method of combating weeds which comprises applying to the weeds, or to a habitat thereof, the compound prepared according to the present invention alone or in the form of a composition containing as active ingredient the compound in admixture with a diluent or carrier.

The present invention further provides crops protected from damage by weeds by being grown in areas in which immediately prior to and/or during the time of the growing the compound prepared according to the present invention was applied alone or in admixture with a diluent or carrier.

The preparative examples which follow are intended to illustrate the process according to the invention in more detail.

PREPARATIVE EXAMPLES

Example 1

(a) Stage 1: $(CH_3)_3C-CO-CO-NH-CO-CH_3$ (IVa)

First 25.6 g (0.25 mol) of acetic anhydride and then 27.8 g (0.25 mol) of pivaloyl cyanide were introduced, in each case at room temperature, into 49.0 g (0.5 mol) of concentrated sulphuric acid, which had been initially introduced into the reaction vessel. After subsequently stirring the reaction mixture for 4 hours, 150 g of icewater were added and the mixture was stirred thoroughly. The reaction product which precipitated was filtered off, washed with 100 ml of water and dried. 37.0 g (86.5% of theory) of trimethylpyruvic acid N-acetylamide were obtained as colorless glistening flakes of melting point 82°–84° C.; content, according to determination by gas chromatography, >98%. No additional purification operations were required for further reactions.

(b) Stage 2:
4-Amino-6-tert.-butyl-3-mercapto-1,2,4-triazin-5(4H)-one (VI)

37.0 g (0.22 mol) of trimethylpyruvic acid N-acetylamide in 150 ml of ethanol were added dropwise to 23.2 g (0.22 mol) of thiocarbohydrazide in 400 ml of 1N HCl and the reaction mixture was subsequently stirred at room temperature for 5 hours. The product which had precipitated was filtered off, washed with water and dried. 41.2 g of the abovementioned product (VI) of melting point 210° C. were obtained, with a content, determined by gas chromatography, of >99% which corresponded to a yield of 95% of theory.

(c) Stage 3:
4-Amino-6-tert.-butyl-3-methylthio-1,2,4-triazin-5(4H)-one (I)

41.2 g (0.206 mol) of 4-amino-6-tert.-butyl-3-mercapto-1,2,4-triazin-5(4H)-one (VI) were introduced into a mixture of 200 g of 45% strength sodium hydroxide solution and 135 g of water, while stirring. After all of the product had dissolved, 34.0 g of methyl iodide were added in a manner such that the internal temperature did not rise above 30° C. When the addition had ended, the reaction mixture was stirred for a further 2 hours at room temperature. The reaction product which had precipitated was then filtered off, washed with 200 ml of water and dried. 35.6 g (81% of theory) of 4-amino-6-tert.-butyl-3-methylthio-1,2,4-triazin-5(4H)-one (I) of melting point 123°–125° C. were obtained.

Several improved processes are available for carrying out the methylation according to stage 3 on a large industrial scale (see, for example, German Published Specification DE-OS No. 2,729,761 and U.S. Pat. Nos. 3,890,317, 3,897,429, 3,905,973 and 4,035,364).

Example 2

(a) Hydrolysis

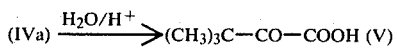

17.1 g (0.1 mol) of trimethylpyruvic acid N-acetylamide (IVa) in 100 ml of 5N HCl were heated to 90° C. for 4 hours. After cooling, the mixture was extracted by shaking with methylene chloride, the methylene chloride phase was extracted with dilute NaOH solution, the alkaline aqueous solution was adjusted to a pH of 1 with concentrated HCl and was extracted by shaking with ethyl acetate and the ethyl acetate extract was then evaporated. 11.9 g (92% of theory) of trimethylpyruvic acid (V) were obtained.

(b) The conversion of trimethylpyruvic acid into the triazinones (IV) and (I) is known (see, for example, U.S. Pat. Nos. 4,113,767 and 4,175,188.

It will be appreciated that the instant specification and examples are set forth by way of illustration and not limitation, and that various modifications and changes may be made without departing from the spirit and scope of the present invention.

We claim:

1. In the preparation of 4-amino-6-tert.-butyl-3-alkylthio-1,2,4-triazin-5(4H)-one of the formula

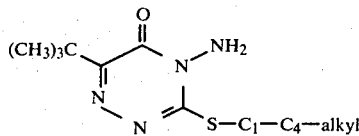

wherein (1) pivaloyl cyanide of the formula

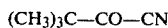

is reacted to form a derivative of pyruvic acid, (2) the pyruvic acid derivative is condensed with thiocarbohydrazide of the formula

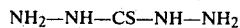

to form 4-amino-6-tert.-butyl-3-mercapto-1,2,4-triazin-5(4H)-one of the formula

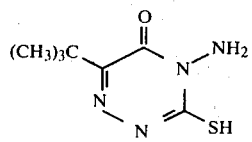

and (3) this is alkylated, the improvement which comprises effecting step (1) by reaction with a carboxylic acid anhydride of the formula

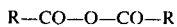

in which R is an optionally substituted aliphatic radical with up to 8 carbon atoms or an optionally substituted phenyl radical, in the presence of a strong acid at a temperature between about −50° and +150° C., and then adding water to the reaction mixture, thereby to form trimethylpyruvic acid N-acylamide of the formula

2. A process according to claim 1, wherein the reaction with pivaloyl cyanide is effected at a temperature between about 0° and 100° C.

3. A process according to claim 1, wherein the molar ratio or pivaloyl cyanide: carboxylic acid anhydride is about 1:0.5–10.

4. A process according to claim 1, wherein the molar ratio of pivaloyl cyanide: carboxylic acid anhydride is about 1:0.8–4.

5. A process according to claim 1, wherein the molar ratio of pivaloyl cyanide: carboxylic acid anhydride is about 1:1–2.

6. A process according to claim 1, wherein the molar ratio of pivaloyl cyanide: strong acid is about 1:0.5–10.

7. A process according to claim 1, wherein the molar ratio of pivaloyl cyanide: strong acid is about 1:0.8–8.

8. A process according to claim 1, wherein the molar ratio of pivaloyl cyanide: strong acid is about 1:1–4.

9. A process according to claim 1, wherein the molar ratio of carboxylic acid anhydride: strong acid is about 1:2.

10. A process according to claim 1, wherein the molar ratio of pivaloyl cyanide: carboxylic acid anhydride: strong acid is about 1:1:2 to 1:2:4.

11. A process according to claim 1, in which R is optionally chlorine-substituted alkyl with 1-4 carbon atoms, or phenyl.

12. A process according to claim 1, wherein the carboxylic acid anhydride is acetic anhydride.

13. A process according to claim 1, wherein the strong acid is an oxyacid.

14. A process according to claim 1, wherein the strong acid is concentrated sulphuric acid.

15. A process according to claim 1, wherein glacial acetic acid, methylene chloride, a dialkyl ether or a diaryl ether is employed as a solvent in the reaction with pivaloyl cyanide.

16. A process according to claim 1, wherein the reaction with pivaloyl cyanide is carried out in the absence of a solvent.

17. A process according to claim 1, wherein the trimethylpyruvic acid N-acylamide formed as an intermediate product is hydrolyzed to trimethylpyruvic acid which is condensed with the thiocarbohydrazide.

18. A process according to claim 1, wherein the condensation with thiocarbohydrazide is effected between about −20° and +150° C.

19. A process according to claim 1, wherein the pyruvic acid derivative and thiocarbohydrazide are employed in approximately equimolar amounts.

20. A process according to claim 1, wherein the condensation with thiocarbohydrazide is effected in the presence of a mineral acid, in an aqueous or aqueous-alcoholic medium.

21. A process according to claim 20, wherein the mineral acid is hydrochloric acid.

22. A process according to claim 1, wherein alkylation is effected with methyl bromide or methyl iodide in the presence of a base at about 0° to 50° C.

23. A process according to claim 22, wherein the base is sodium hydroxide.

24. A process according to claim 10, wherein the carboxylic acid anhydride is acetic anhydride, the reaction with pivaloyl cyanide is effected at a temperature between about 0° and 100° C., the strong acid is concentrated sulphuric acid, the condensation with thiocarbohydrazide is effected with an approximately equimolar amount of the pyruvic acid derivative at about −20° to 150° C. in the presence of hydrochloric acid in an aqueous or aqueous-alcoholic medium, and alkylation is effected with methyl bromide or methyl iodide in the presence of sodium hydroxide at about 0° to 50° C.

* * * * *